United States Patent [19]

Harrell

[11] Patent Number: 5,002,071

[45] Date of Patent: Mar. 26, 1991

[54] INJECTABLE SOFT TISSUE AUGMENTATION MATERIALS FROM THE PLACENTA AND THEIR METHOD OF MANUFACTURE

[75] Inventor: Carl R. Harrell, Houston, Tex.

[73] Assignee: Research Development Foundation, Carson City, Nev.

[21] Appl. No.: 413,885

[22] Filed: Sep. 27, 1989

Related U.S. Application Data

[63] Continuation of Ser. No. 174,667, Mar. 29, 1988, abandoned.

[30] Foreign Application Priority Data

Apr. 3, 1987 [GB] United Kingdom ............... 8708009

[51] Int. Cl.$^5$ .................................... A61B 19/00
[52] U.S. Cl. .................................... 128/897; 128/898; 604/49; 623/8; 623/11; 623/15; 623/66; 424/520, 583
[58] Field of Search .............. 623/16, 1, 8, 11, 15, 623/66; 128/897, 898; 424/105, 95; 604/48, 49, 54

[56] References Cited

U.S. PATENT DOCUMENTS

| | | | |
|---|---|---|---|
| 1,699,479 | 0/0000 | Scott | 424/105 |
| 4,042,117 | 2/1987 | Nguyen et al. | 623/11 |
| 4,361,552 | 11/1982 | Baur | 424/105 |
| 4,446,234 | 5/1984 | Russo et al. | 435/29 |
| 4,699,788 | 10/1987 | Catsimpgolas et al. | 424/104 |
| 4,795,459 | 1/1989 | Jauregui | 623/1 |
| 4,801,299 | 1/1989 | Brendel et al. | 623/1 |
| 4,863,733 | 9/1989 | Startz et al. | 424/101 |
| 4,865,602 | 9/1989 | Smestad et al. | 623/16 |
| 4,873,222 | 10/1989 | Arai et al. | 514/21 |

FOREIGN PATENT DOCUMENTS 2110531 6/1983 United Kingdom .

*Primary Examiner*—C. Fred Rosenbaum
*Assistant Examiner*—Mark O. Polutta
*Attorney, Agent, or Firm*—James F. Weiler

[57] ABSTRACT

Disclosed is a soft tissue augmentation material from human placenta homogenized to pass through a surgical needle, preferably a 30 gauge surgical needle, and crosslinking collagen molecules of the material by gamma irradiation. Also disclosed are methods of making the injectable soft tissue augmentation material and using it in human beings.

21 Claims, No Drawings

INJECTABLE SOFT TISSUE AUGMENTATION MATERIALS FROM THE PLACENTA AND THEIR METHOD OF MANUFACTURE

CROSS-REFERENCE TO RELATED APPLICATION

The present application is a continuation of application Ser. No. 174,667, filed Mar. 29, 1988, abandoned in favor of this application.

FIELD OF THE INVENTION

The present invention is in the field of injectable material for soft tissue augmentation.

BACKGROUND OF THE INVENTION

The idea of using an injectable material for soft tissue augmentation developed soon after the invention of the hypodermic needle. Various products have been injected into the human body for correction of soft tissue defects including paraffin, petrolatum, vegetable oils, lanolin, bees wax, silicone, and more recently, collagen.

Paraffin was first used by Gersury in 1899[1] who injected it into the scrotum of a young man to replace resected testicles. He later used paraffin to correct facial contour defects. During the period of 1900–1914, the use of paraffin injections became popularized.

Heidingsfeld in 1906[2] described the paraffinoma. Injected paraffin forms many widely diffused droplets in the tissues. Phagocytosis by macrophages and giant cells occurs, followed by hyalin necrosis of fibrovascular septa, proliferation of fibroblasts, and development of scar tissue containing oil globules and cysts lined by foreign body giant cells.

Clinically, edema and scar formation occurred, sometimes followed by ulceration. The use of injectable paraffin was discontinued in the United States around World War I, but continued to be used in the Far East until the 1950's.

Silicones were the next material to be injected into humans on a large scale. Conway and Goulian reported on the use of silicone injections into the breast and face in 1963[3]. Some people were using the "Sakurai" formula, a silicone fluid, adulterated with an additive for better fixation[4]. Dow Corning developed a more purified "medical grade 360 liquid silicone" and, although this product was not originally intended to be injected, it was soon used for human injections around the world.

The first reports of complications of injected silicone including foreign body granulomas occurred in 1964[5]. In 1965, Ben-Hur and Neuman[6] described the siliconoma which was a tumor-like formation developing after the injection of silicone 360 in rats.

In 1965, the U.S. Food and Drug Administration (F.D.A.) determined that the clinical use of injectable silicone was a "drug use" and authorized seven investigators to employ silicone fluid as a soft tissue substitute. After reviewing their clinical experiences with injectable silicone - Dow Corning - MDX 4.4011, they concluded that silicone MDX 4.4011 can provoke an inflammatory reaction resulting in redness and ecchymosis which can be controlled with antibiotics and corticosteroids. Partial resorption and migration can occur but can be avoided by repeated injections of small amounts[7,8,9,10,11,12,13]. Although few complications have been reported with MDX 4.4011, many complications have been described after injection of liquid silicone with an unknown grade of purity[14]. Although a few individuals are still injecting silicone with good results and few complications, the unforgiving nature of the material if used incorrectly will probably prevent its widespread use.

Bovine collagen has recently gained widespread use as an injectable material for soft tissue augmentation.

Collagen is the principal extracellular structural protein of the animal body. At least seven types of mammalian collagen have been described. Their common characteristic is a three stranded helix, consisting of 3 polypeptide chains, called alpha-chains. All chains have the same configuration, but differ in the composition and sequence of their aminoacids. This leads to different types of alpha chains, but they all have glycine in every third position of the aminoacid sequence. This allows the helical conformation to occur. Type I collagen is composed of 2 $alpha_1$-chains and one $alpha_2$-chains and is the principal extracellular material of skin, tendon, and bone. When clinicians speak of "collagen," they are usually referring to Type 1. Type II collagen is found in cartilage and the vitreous humor. Type III collagen is present in rapidly growing tissue, particularly juvenile and healing skin. Collagen Types IV and V are found in epithelial basement membrane[14].

The major molecular species beside collagen that are found in the extracellular matrix include the noncollagenous structural glycoproteins, elastin, and the proteoglycans. The structural glycoproteins consist of fibronectin and laminin. Fibronectin is found in both the plasma and tissue forms and is capable of interacting with other components of the extracellular matrix. Recently, Wartiovaara proposed that another function of fibronectin is to opsonize collagen or fibrin and, by this mechanism, to regulate the cellular digestion of these substrates[15]. Laminin is found in all basement membranes. Proteoglycans are characterized by a protein core linked to glycoaminoglycan side chains[15,16,17,18].

When using collagen as a biomaterial, it is important to use it in its purest and crystalline form to eliminate the noncollagenous proteins that are far more potent antigens. Once the inflammatory cycle is stimulated, the resorption of collagen occurs by the infiltrating inflammatory cells, principally macrophages and, to a lesser extent, granulocytes. These cells contain collagenase which acts to digest collagen[19]. Houch and Chang demonstrated that skin collagen was chemotactic itself and became even more active by digestion with tissue collagenase into smaller peptide fragments[20]. Chemotropism is the attraction of living protoplasm to chemical stimuli whereby the cells are attracted (positive hemotaxis) or repelled (negative chemotaxis) by acids, alkalis or other bodies exhibiting chemical properties. Postlethwaite et al[21] showed that various types of collagens, their alpha-chains, as well as small peptides formed by collagenase digestion were all chemotactic to dermal fibroblasts. They concluded that the chemotactic migration of fibroblasts into the site of tissue injury or theoretically injected collagen can be regulated by the solubilized collagen or its degradation products. Thus, a collagen implant would not remain dormant in the tissue but a complex series of events may occur. First, the collagen implant could be invaded by inflammatory and fibroblasts and, while being continuously resorbed, it could promote an inflammatory reaction by chemotactic properties of its degradation products. Thus, the area of collagen metabolism is not only important for collagen and other soft tissue injectable materials, but also to both normal and abnormal wound healing (i.e. hypertrophic scarring and keloids)[19,20,21].

The injectable collagen that recently gained widespread use was given marketing clearance as a device (not a drug) by the Food and Drug Administration in 1981. This material sold under the name Zyderm® Collagen Implant is a purified bovine collage. About 95% consists of Type I collagen and the remaining 5%, Type III collagen. The collagen undergoes proteolytic hydrolysis of its telopeptide portion to decrease its antigenicity. The material is suspended in physiologic saline buffer, and 0.3% lidocaine is added and the material is packaged in syringes ready for injection through small gauge needles.

The most immediate concern to most plastic surgeons is the fate of bovine collagen after injection. Zyderm I® with 35 mg/ml of collagen is rapidly degraded by tissue collagenases and resorbed within months. Zyderm II® with 65 mg/ml of collagen and, thus, almost twice the concentration of collagen, is longer lasting but follows the same fate as Zyderm I®. Zyplast® was most recently introduced containing 35 mg/ml of collagen cross-linked with glutaraldehyde. Zyplast® also is ultimately degraded over time. Kligman[22] recently compared the biological fat of Zyderm® collagen and Zyplast® collagen when implanted into the back of human volunteers. They reported that, while Zyderm® collagen was apparently resorbed by host tissue within months of implantation, Zyplast® was more persistent. Fibroblasts infiltrated the Zyplast® collagen and deposited host collagen. Burke et al[23] reported that Zyderm® collagen stimulates a response which results in implant degradation and replacement by newly generated host collagen.

One additional area of confusion about Zyderm I® collagen, Zyderm II® collagen and Zyplast® collagen is the percentage of collagen in each. Zyderm I® collagen and Zyplast® collagen have 35 mg/ml, (3.5% collagen) while Zyderm II® has 65 mg/ml (6.5% collagen).

A small percentage of patients receiving either Zyderm I® collagen, Zyderm II® collagen or Zyplast® collagen, hereafter referred to as bovine collagen implants (BCI), have developed adverse reactions of an immune nature. The safe use of these implants is based on the reported low immunogenicity of the bovine collagen. It is, however, contraindicated in patients with a history of autoimmune disease. Skin tests are required before receiving the BCI. Only patients with negative skin tests after 4 weeks should have the treatment injections. The Collagen Corporation indicates that approximately 3% of the patients have a positive skin test reaction characterized by edema, induration, erythema, pruritus or tenderness at the injection site. Adverse generalized treatment reactions have been quoted from less than 1% to greater than 5%. They are characterized by urticaria, myalgias, arthralgias and one anaphylactoid reaction [23,24]. A dramatic increase in the incidence of anti-BCI antibodies in the circulation of patients with adverse BCI-treatment reactions has been noted compared with serum samples from untreated individuals or treated patients suffering adverse reactions. BCI is a weak antigen but still is a foreign protein. It has been treated in such a way to cleave the telopeptides to make it less immunogenic but the helical portion of the molecule retains its antigenic loci. The dominant structures recognized by the cell-mediated immunological mechanism appear to reside within the triple helical body of the collagen molecules. There has been a major concern about repeated exposure of patients to these antigens and their long-term effects[24,25,26].

In summary, due to the shortcomings of the BCI, including the lack of persistence, need for repeated injections and serious concern over adverse reactions, newer injectable materials for soft tissue augmentation are needed. The present invention is directed to injectable materials for soft tissue augmentation and their methods of manufacture which overcome shortcomings of BCI and other injectable materials of the prior art.

DESCRIPTION OF PRIOR ART

In addition to the prior art discussed above, U.S. Pat. No. 4,361,552 discloses a method of treating a wound or burn with an amnion dressing from any suitable animal species (human, cattle, pigs, etc.) fixed or stabilized by toxic chemical agents, such as glutaraldehyde solutions or other fixing or tanning solutions, so that the proteins thereof are cross-linked. A number of U.S. patents are cited and listed in this patent.

U.K. Patent Application No. 8133375, published 22 June, 1983 discloses a substantially amnion-free preparation for use in the treatment of wounds derived from a culture medium in which amnion has been cultured, the amnion preferably being human amnion.

SUMMARY OF THE INVENTION

The present invention is directed to an injectable soft tissue material in which th problems associated with xenogeneic bovine sources have been eliminated, the problem of lack of persistence and need for repeated injection has been addressed to make it less susceptible to degradation, and for which the starting material is available in unlimited quantities and at low cost.

The injectable soft tissue augmentation material is from human placenta and consists of insoluble amnion, soluble amnion, soluble chorion and combinations thereof, homogenized to pass through a surgical needle. Preferably, the homogenized material should pass through a 30 gauge surgical needle to avoid discomfort, and, if desired, an analgesia can be added. In one aspect of the invention, the material is irradiated at a minimum of 0.20 M rads for sterilization and cross-linking with a preferred range of from about 0.25 M rads to about 2.0 M rads. The presently preferred injectable soft tissue augmentation material is irradiated soluble amnion.

The method of the invention of making such an injectable soft tissue material comprises homogenizing a material from human placenta consisting of insoluble amnion, soluble amnion, soluble chorion and combinations thereof sufficiently so that it will pass through a surgical needle, and preferably a 30 gauge surgical needle, sterilizing the collagen molecules, preferably by gamma irradiation which also cross-links them. A minimum of 0.20 M rads is necessary to sterilize these materials, and the presently preferred range is from about 0.25 M rads to 2.0 M rads. If desired, an analgesic can be added to the homogenized injectable soft tissue material.

The method of the invention of correcting soft tissue contour defects is by injecting the injectable soft tissue material of the invention in a patient. Advantageously, a number of injections of small amounts of the soft tissue material are possible since even small amounts persist. This provides a greater host-implant interface and allows faster assimilation into the tissue since the center of the implant is not far from host tissue influences.

Accordingly, it is an object of the present invention to provide an injectable sterilized soft tissue material in which adverse allergic reactions are eliminated, which has long-term persistence and little inflammation, which can be injected through a 30 gauge needle, and in one aspect of the invention gamma irradiation is used to both sterilize the material and increase the amount of cross-linking of the collagen without using toxic cross-linking agents.

It is a further object of the present invention to provide an injectable sterilized soft tissue material from human placenta consisting of insoluble amnion, soluble amnion, soluble chorion, and combinations thereof, homogenized sufficiently to pass through a surgical needle, such as a 30 grade needle, and in one aspect of the invention is purified and cross-linked by gamma irradiation without the use of toxic chemicals.

A further object of the present invention is the provision of making an injectable soft tissue material in which adverse allergic reactions are eliminated in which gamma irradiation is used to both sterilize the material and increase the amount of cross-linking, and in which by varying the amount of cross-linking, the amount of tissue persistence can be regulated.

A further object of the present invention is the provision of a method of making a soft injectable augmentation material having the above-mentioned advantages by homogenizing insoluble amnion, soluble amnion, soluble chorion, or combinations thereof from a human placenta so that the material passes through a surgical needle, preferably a 30 gauge surgical needle, and cross-linking collagen molecules of the material by gamma irradiation of at least 0.20 M rads and, preferably, in the range of from 0.25 M rads to 2.0 M rads.

It is a further object of the present invention to provide a method of recontouring soft tissue by injecting into humans material from a human placenta comprising insoluble amnion, soluble amnion, soluble chorion, or combinations thereof, sterilized and homogenized to the extent that it can be injected by a surgical needle, and preferably a 30 gauge surgical needle and in one aspect of the invention sterilized and having its collagen molecules cross-linked by gamma irradiation.

A still further object of the invention is the provision of such a method of recontouring soft tissue by injection into humans such injectable material in small amounts to provide good host implant interface and allow faster assimilation into the tissue and yet have good persistence.

Other and further objects, features, and advantages of the invention appear throughout the specification and claims.

PRESENTLY PREFERRED EMBODIMENTS OF THE INVENTION

Human fetal membranes were selected as the starting material for the injectable soft tissue augmentation material into human beings for recontouring soft tissue since they eliminate the allergic problems seen with xenogeneic sources, i.e. bovine, human placentas are available in relatively unlimited quantities and are a rich source of collagen, placentas are available at a low cost, and amnion has had a long-history of medical uses beginning almost 90 years ago for a wide variety of medical and surgical applications.

The fetal membranes are complex biochemical structures that can be developed into one or several different soft tissue injectable materials. These have physical and biological characteristics that can be modified to fulfill various clinical needs.

The preferred human fetal membranes are insoluble amnion, soluble amnion, soluble chorion or combinations of them. They are homogenized to pass through a surgical needle. While injecting the soft tissue augmentation materials through a 25 gauge surgical needle is satisfactory for clinical purposes, to avoid discomfort, preferably the material is homogenized so that it passes can be injected through a 30 gauge surgical needle.

In one aspect of the invention, the injectable material is cross-linked by gamma irradiation without the use of chemical cross-linking agents, such as glutaraldehyde, which are toxic. The gamma irradiation should be a minimum of 20 M rads to sterilize the material Since all bacteria, fungi and viruses, including AIDS, are destroyed at 0.20 M rads. Preferably, the material is irradiated from 0.25 to 2.0 M rads to sterilize and cross link the collagen molecules.

If desired, an analgesic, such as lidocaine can be added to the injectable material.

In making the soft injectable material, fresh placentae were collected and the amnion is manually separated from the chorion, such as by finger separation. Both the amnion and the chorion are then cleaned of any remaining blood clots or debris. For short-term storage, the amnion and the chorion are placed in an antibiotic solution, for example, linomycin 3 gms/10 ml, amphotericin B 50 mg/10 ml, neomycin sulfate 0.5 gm/10 ml, polymyxin B sulfate 500,000 units/10 ml in 1 liter of normal saline until processed.

Collagen was extracted using limited proteolytic digestion with pepsin. In brief, tissue was homogenized in 0.5 M acetic acid, the pH was adjusted to 2.5 with HCl and the preparation was digested twice with pepsin (10 mg pepsin/gm wet weight tissue) overnight. A combination method of selective precipitation from neutral salt solvent and acid solvents was used to purify the collagen. Purified collagen was reconstituted by dialysis against low ionic strength sodium phosphate buffer (pH 7.2) at 15°–17° C. Lidocaine was added to a final concentration of 0.3%. All procedures were carried out at 4°–8° C. although other suitable temperatures can be used.

INSOLUBLE AMNION PROCESSING

A presently preferred method of processing the amnion comprises decanting the antibiotic from the amnion, adding 5 ml of cold distilled water to each amnion, and homogenizing the amnion approximately 15 minutes in polytron. The homogenized amnion is then centrifuged at 8,000×5 for 15 minutes at 4° C., the supernatant is discarded, and the precipitant is washed to remove the lipids, such as 5 times with acetone. The precipitant is then weighed, and pepsin (Sigma, 1:10,000, from porcine stomach mucosa) 3.0 molar acetic acid per amnion was added, 15 ml or more if extra large amnions, and the precipitant was homogenized for approximately 5 minutes in polytron.

The mixture was allowed to stand for 18 hours at 4° C., centrifuged at 100,000×g for 1 hour at 4° C., the supernatant was discarded, the precipitant weighed and then the pepsin and homogenization steps were repeated and the supernatant discarded.

SOLUBLE AMNION PROCESSING

A presently preferred way of processing soluble amnions comprises rinsing the antibiotics from the amnions with deionized water, adding 5ml of cold distilled water to each amnion, homogenizing for approximately 15 minutes in polytron and centrifuging at 8,000×g for 15 minutes at 4° C. The supernatant was discarded and lipids were removed from the precipitate by washing with acetone three times and precipitate was weighed.

Pepsin (Sigma, 1:10,000, from porcine stomach mucosa) was added to the precipitate (1:100 w/w) and 100 ml of 0.5 molar acetic acid per amnion was added, more if the amnions are extra large, and then homogenized for approximately 10 minutes in polytron. The pepsin was allowed to extract collagen from the precipitate for 18 hours at 4° C. and then centrifuged at 100,000×g for 1 hour at 4° C. retaining both the precipitate and the supernatant. The supernatant is again weighed, and the steps of pepsin and acetic acid addition, homogenization, pepsin extraction of collagen and centrifuging are then repeated.

The supernatants from the first and second extractions are combined and 10-molar NaOH is added drop wise to adjust the pH to from 7.0 to 7.2. The mixture is permitted to stand for 2 hours at 4° C., centrifuged at 100,000×g for 45 minutes at 4° C. and the precipitate is discarded. NaCL to 3.0-molar is added to the supernatant and permitted to stand for 2 hours at 4° C., centrifuged at 100,000×g for 45 minutes at 4° C. and the precipitate is weighed and lidocaine to 0.3% is added.

SOLUBLE AMNION PROCESSING WITH FURTHER PURIFICATION

A presently preferred method of soluble amnion processing and further purification comprises rinsing the antibiotic from the amnion with deionized water, the amnions are cut to approximately 2 cm×2 cm and washed briefly with acetone, soaked in 0.5 M acetic acid (pH adjusted to 2.5 with HCl), homogenized with polytron for about 15 minutes, pepsin is added (1:100 pepsin/set tissue) (1 mg pepsin/1 ml solution) and stirred at 4° C. overnight, centrifuged as indicated above, the supernatant being retained. Pepsin was again added as indicated previously and stirred at 4° C. overnight, centrifuged and the supernatant from both centrifuging steps were combined and NaCL was added to 2 M and permitted to stand overnight at 4° C. and again centrifuged, the supernatant discarded and the precipitate retained.

The precipitate was purified by dissolving it in 0.5 M acetic acid, centrifuging, precipitate discarded, NaCL to 2 M was added to the supernatant, and it was permitted to stand overnight at 4° C., again centrifuged with the supernatant discarded. The resulting precipitate was dissolved in 0.5 M acetic acid, again centrifuged, and the precipitate discarded. The supernatant was dialysed against 0.02 M $Na_2HPO_4$ thoroughly for 48 hours with frequent dialysis fluid exchanges, centrifuged, the supernatant discarded, the precipitate weighed and solid lidocaine HCl was added to 0.30% with mechanical agitation.

CHORION PROCESSING

In a presently preferred method of processing soluble chorion the antibiotics were rinsed from the chorion with deionized water, the chorion was cut to approximately 2 cm×2 cm units and washed briefly with acetone and then soaked into 0.5 M acetic acid that had been adjusted to pH 2.5 with HCl. The tissue was then homogenized with polytron to fine particles for about 15 minutes, pepsin added and centrifuged as indicated above with the supernatant being retained. The pepsin and centrifuge steps were then repeated, the supernatant of each of these steps were combined and NaCL to 2 M was added and permitted to stand overnight at 4° C. and then centrifuged again with the supernatant discarded.

For purification, the precipitate was dissolved into 0.5 M acetic acid, centrifuged and the precipitate discarded. NaCL to 2 M was added to the supernatant and permitted to stand overnight at 4° C., then again centrifuged and the supernatant discarded. The precipitate was dissolved into 0.5 M acetic acid, centrifuged, dialysed against 0.02 M $Na_2HPO_4$ thoroughly for 48 hours with frequent dialysis fluid exchanges, again centrifuged, the supernatant discarded and the precipitate weighed. Solid lidocaine HCl was added to 0.30% to the precipitate with mechanical agitation.

CROSS-LINKING AND STERILIZING 15 cc of each of the foregoing resulting precipitates was placed in 20 cc serum bottles with crimp closures and placed in $CE^{137}$ radioactive source for varying lengths of time in order for them to receive 0.25 M rads, 0.5 M rads, 1.0 M rads, and 2.0 M rads which served the dual purpose of sterilizing the material and cross-linking the collagen.

EXAMPLE 1

Several groups of collagen extracts were reconstituted in phosphate buffered saline and place in glass tubes and irradiated in 1779 curies Cesium gamma rays source at a dose of 1000 rads/minute. The dosage was 0.25 M rads. Irradiation was carried out at room temperature.

TABLE 1

The groups examined were as follows:

| Group |
| --- |
| 1. Soluble amnion with 0.25 M rads. |
| 2. Soluble amnion without radiation. |
| 3. Insoluble amnion with 0.25 M rads. |
| 4. Insoluble amnion without radiation. |
| 5. Insoluble amnion + soluble amnion (1:1) with 0.25 M rads. |
| 6. Insoluble amnion + soluble amnion (1:1) without radiation. |
| 7. Soluble chorion with 0.25 M rads. |
| 8. Soluble chorion without radiation. |
| 9. Soluble chorion + soluble amnion (1:1) with 0.25 M rads. |
| 10. Soluble chorion + soluble amnion (1:1) without radiation |

Samples from each group were sent for aerobic, anerobic, and fungal cultures. All groups showed no growth both before as well as after irradiation.

120 young Sprague-Dawley rats weighing between 200-300 grams were used for the animal injections. Twelve groups of animals were studied including groups injected with Zyderm II ® and Zyplast ®. There were 10 rats in each group. 0.2 ml of injectable material was injected percutaneously into their backs below the panniculus carnosus in three separate sites. Samples were harvested from 5 rats in each group at one month and six months.

Specimens were fixed in 10% buffered formalin and later embedded in paraffin. Serial sections were made and stained with hematoxylin-eosin (H&E). Results were compared using an independent staff pathologist.

The histological evaluation of implants revealed similarities of all the experimental groups with the exception of the insoluble amnion which will be subsequently discussed. Specifically, no inflammatory reaction was evident and no encapsulation occurred. Fibrocytic ingrowth is present at 30 days and is more advanced centripetally at 180 days. Neovascularization was present in a variable extent at 180 days. The degree of both fibrocytic ingrowth and neovascularization was greater than that found with Zyderm II ® and Zyplast ® at 180 days.

The insoluble amnion group also demonstrated no inflammation or encapsulation but marked neovascularization and fibrocytic ingrowth. An additional observation was the presence of a few adipocytes at 30 days. At 180 days the adipocytes that first appeared on the periphery of the implant had become dispersed throughout the implant. This phenomena has been observed by others[27,28].

A quantitative analysis (measuring exact dimensions of persisting implant) was very difficult to perform. Therefore, a preliminary qualitative study of persistence was performed. Simply, the number of implants visibly present in the rats surviving at 6 months was counted. Table 2 demonstrates that the soluble amnion group showed very good persistence at 6 months The nonirradiated soluble amnion had all implants present at 6 months and the irradiated soluble amnion had 11 out of 15. The insoluble group also showed good persistence in both the irradiated and nonirradiated groups. Some of the groups having combinations of materials especially soluble chorion had less persistence after irradiation.

TABLE 2

PERSISTENCE OF SOFT TISSUE AUGMENTATION INJECTIONS AFTER 6 MONTHS ANIMAL EXPERIMENT GROUP 1-10, ZYDERM II ® and ZYPLAST ®

| | 1 Group | 2 Concentration of Collagen (mg/ml) | 3 Number of Rats Survival/ Injected | 4 Injections Present After 6 Months/ Total Number Injected |
|---|---|---|---|---|
| 1* | Sol. Am | 51 | 5/5 | 11/15 |
| 2 | Sol. Am | 37.2 | 5/5 | 15/15 |
| 3* | Ins. Am | 23.5 | 5/5 | 9/15 |
| 4 | Ins. Am | 22.2 | 5/5 | 13/15 |
| 5* | Ins. Am & Sol. Am | 40.4 | 4/5 | 3/12 |
| 6 | Ins. Am & Sol. Ch. | 40.5 | 5/5 | 15/15 |
| 7* | Sol. Ch. | 40.3 | 5/5 | 2/15 |
| 8 | Sol. Ch. | 55.8 | 2/5 | 6/6 |
| 9* | Sol. Am & Sol. Ch. | 52.8 | 3/5 | 0/9 |
| 10 | Sol. Am & Sol. Ch. | 58.6 | 5/5 | 15/15 |
| 11 | Zyderm II ® | 65 | 2/5 | 6/6 |
| 12 | Zyplast ® | 35 | 4/5 | 12/12 |

Note:
*Sample was irradiated with 0.25 M rads gamma irradiation.

Numerous histological studies at intervals from one to six months have shown fibrocytic ingrowth as well as neovascularization with no inflammation. The observation of adipocyte incorporation into the insoluble amnion implants is very interesting but we are unable to explain why it occurs. Stromal infiltration of fat has been previously observed by others[27,28] and is a strange phenomenom of an obscure nature. Accumulation of increased amounts of fat occasionally occurs within the interstitial tissue of certain tissues and organs. Robins and Angel[29] offer an explanation that presumably the multipotential fibroblasts in the interstitium become filled with lipid and in effect are converted to "obese" fat cells. Stromal infiltration by fat tends to be associated with obesity or with atrophy of parenchymal cells, but the correlations are imperfect. The heart and pancreas are most often involved.

The fact that there were only a few adipocytes at 30 days and an increased number at 180 days would seem to indicate a phenomenom occurred similar to that described above. The stimulation of new adipocyte deposition offers an interesting and new possible avenue to soft tissue augmentation.

Biochemical analysis has demonstrated the purity of the injectable human amnion and chorion collagen. The PAGE electrophoresis and amino acid assay have shown HAC to have a typical collagen electrophoresis pattern and an amino acid composition of a mixture of Type I and III collagen.

The bacterial collagenase digestion results demonstrated that no noncollagen protein existed in injectable human amnion and chorion collagen. By immunoblotting examination, no residual fibronectin and laminin was detected in the collagen product of the present invention. We believe that the high purity of HAC contributed to the low immunological response in the rat model.

The proportion of type III collagen to type I collage is much larger in injectable human amnion collagen (43:57) than in Zyderm ® and Zyplast ® (5:95). Type III collagen has inter-chain disulfate bonds, whereas type I collagen does not, so after treatment by pepsin extraction, type I collagen exists in the form as a mixture of $\alpha$, $\beta$ and $\gamma$ chains while type III collagen exists mainly in the $\gamma$ form. It is postulated that the greater the cross-linking, the longer the persistence of type III collagen in amnion collagen would appear as a factor of importance in considering the most efficacious collagen for soft tissue augmentation.

Cell biology studies demonstrated that gamma irradiated human amnion collagen had no cytotoxic effect on cell growth and on cell behavior. Cells growing on irradiated human amnion collagen substrate have a normal morphological appearance and active pseudopodia. In cell number and [$^3$H] incorporated experiments, no significant differences were found among the cells growing on irradiated human amnion collagen and Vitrogen ®, Zyderm ® and nonirradiated human amnion collagen.

The biochemical characterization of the various injectable human amnion collagens for purity assessment, and ratio of collagen types, included polyacrylamide gel electrophoresis (PAGE), densitometry, collagenase digestion, amino acid analysis (AAA), immunoblotting, electron-microscopy (EM), collagenase sensitivity assay, and hydroxyproline assay. No detailed description is given or deemed necessary of these various procedures since they are all conventional.

Good results are obtainable with gamma irradiation at a minimum of 0.20 M rads and in the range of 0.25 M rads and 2.0 M rads. Any combination of the amnions and chorion can be employed with good results.

The foregoing animal study is an excellent model for injection of the injectable material into human beings.

The present invention, therefore, is well suited and adapted to attain the objects and ends and has the features and advantages mentioned as well as others inherent therein.

While presently preferred examples have been given for the purpose of disclosure, changes can be made therein which are within the spirit of the invention as defined by the scope of the appended claims.

What is claimed is:

1. An injectable soft tissue augmentation material comprising,
   a sterilized mixture of type I and type III collagen extracted by proteolytic digestion from the group consisting of insoluble amnion, soluble amnion, soluble chorion from human placenta and combinations thereof,
   homogenized to pass through a surgical needle.

2. The injectable soft tissue augmentation material of claim 1 where,
   the collagen is homogenized to pass through a 30 gauge surgical needle.

3. The injectable soft tissue augmentation material of claim 1 where,
   the selected collagen is from soluble amnion.

4. The injectable soft tissue augmentation material of claim 1 where,
   the collagen is cross-linked by gamma irradiation.

5. The injectable soft tissue augmentation material of claim I where,
   the gamma irradiation is a minimum of 0.20 M rads.

6. The injectable soft tissue augmentation material of claim 4 where,
   the gamma irradiation is in the range of from 0.25 M rads to 2.0 M rads.

7. The injectable soft tissue augmentation material of claim I includes,
   an analgesic.

8. A method of making an injectable soft tissue material comprising,
   sterilizing a mixture of type I and type III collagen extracted by pepsin digestion selected from the group consisting of insoluble amnion, soluble amnion, soluble chorion from human placenta and combinations thereof, and
   homogenizing the material sufficiently to pass through at least a 25 gauge surgical needle.

9. The method of making the injectable soft tissue material of claim 8 comprising,
   cross-linking molecules of the collagen by gamma irradiation.

10. The method of claim 9 where,
    the gamma irradiation is a minimum of 0.20 M rads.

11. The method of claim 9 where,
    the gamma irradiation is in the range of 0.25 M rads to 2.0 M rads.

12. The method of making the injectable soft tissue material of claim 8 including,
    adding an analgesic to the homogenized collagen.

13. A method of augmenting soft tissue in a human being comprising,
    injecting into the human being the collagen of claim 1.

14. A method of augmenting soft tissue in a human being comprising,
    injecting into the human being the collagen of claim 2.

15. A method of augmenting soft tissue in a human being comprising,
    injecting into the human being the collagen of claim 3.

16. A method of augmenting soft tissue in a human being comprising,
    injecting into the human being the collagen of claim 4.

17. A method of augmenting soft tissue in a human being comprising,
    injecting into the human being the collagen of claim 5.

18. A method of augmenting soft tissue in a human being comprising,
    injecting into the human being the collagen of claim 6.

19. A method of augmenting soft tissue in a human being comprising,
    injecting into the human being the material of claim 7.

20. The injectable soft tissue augmentation material of claim 1 where,
    the proteolytic digestion is with pepsin.

21. A method of augmenting soft tissue in a human being comprising,
    injecting into the human being the collagen of claim 7.

* * * * *

UNITED STATES PATENT OFFICE
CERTIFICATE OF CORRECTION

Page 1 of 2

Patent No. 5,002,071          Dated  March 26, 1991

Inventor(s)  Carl R. Harrell

It is certified that error appears in the above-identified patent and that said Letters Patent is hereby corrected as shown below:

The superscript numerals at the following locations should be deleted:

Column 1, lines 23, 28, 43, 45, 50, 51, 65, and 68.
Column 2, lines 37, 46, 49, and 54.
Column 3, lines 2, 24, 31, and 58.
Column 4, line 3.
Column 8, line 22.
Column 9, line 21.
Column 10, lines 5, 9, and 55.

Column 3, line 7, "collage." should read --collagen--.

Column 4, line 30, "th" should read --the--.

Column 6, line 15, "Since" should read --since--.

Column 8, line 31, "place" should read --placed--.

Column 9, line 28, "months" should read --months.--.

Column 10, line 18, "phenomenom" should read --phenomenon--.

UNITED STATES PATENT AND TRADEMARK OFFICE
CERTIFICATE OF CORRECTION

PATENT NO.   : 5,002, 071
DATED        : March 26, 1991
INVENTOR(S)  : Carl R. Harrell It is certified that error appears in the above-indentified patent and that said Letters Patent is hereby corrected as shown below:

Column 10, line 37, "collage" should read --collagen--.

Signed and Sealed this

Twenty-eighth Day of September, 1993

Attest:

BRUCE LEHMAN

Attesting Officer

Commissioner of Patents and Trademarks